United States Patent [19]

Voelker et al.

[11] Patent Number: 5,435,170
[45] Date of Patent: Jul. 25, 1995

[54] METHOD AND APPARATUS FOR FLUID QUALITY SENSING

[76] Inventors: Paul J. Voelker, 2494 Benchmark Ave., Fremont, Calif. 94536; Joe D. Hedges, 120 Corona Way, Portola Valley, Calif. 94028

[21] Appl. No.: 176,393

[22] Filed: Dec. 30, 1993

[51] Int. Cl.⁶ .................... G01N 27/26; G01N 33/30
[52] U.S. Cl. .................... 73/53.05; 204/153.1; 204/409; 324/663; 324/698; 324/449; 422/82.01; 422/82.02
[58] Field of Search ............... 73/53.01, 53.05, 61.41, 73/61.42; 324/663, 698, 446, 448, 439, 449; 422/82.01, 82.02; 204/400, 409, 410, 421, 422, 153.1

[56] References Cited

U.S. PATENT DOCUMENTS

| | | | |
|---|---|---|---|
| 2,862,859 | 12/1958 | Grosskopf | 204/153.1 |
| 3,182,255 | 5/1965 | Hopkins et al. | 324/666 |
| 3,410,780 | 11/1968 | Holden | 204/153.1 |
| 4,007,629 | 2/1977 | Hochstein | 73/53.05 |
| 4,443,754 | 4/1984 | King | 324/662 |
| 4,606,222 | 8/1986 | Stockmeyer | 204/153.1 |
| 4,646,070 | 2/1987 | Yasuhara et al. | 340/603 |
| 4,733,556 | 3/1988 | Meitzler et al. | 73/53.05 |
| 4,764,258 | 8/1988 | Kauffman | 204/153.1 |
| 4,791,374 | 12/1988 | Yodice et al. | 204/153.1 |
| 4,952,868 | 8/1990 | Scherer, III | 324/664 |
| 5,071,527 | 12/1991 | Kauffman | 324/439 |
| 5,089,780 | 2/1992 | Megerle | 324/698 |
| 5,141,717 | 8/1992 | McRae | 73/61.41 |

OTHER PUBLICATIONS

Mike Allen, "Car Clinic", *Popular Mechanics*, Aug. 1993, p. 71.

Primary Examiner—Hezron E. Williams
Assistant Examiner—Michael J. Brock
Attorney, Agent, or Firm—Skjerven, Morrill, MacPherson, Franklin & Friel; Norman R. Klivans

[57] ABSTRACT

A method and apparatus for determining the quality of a lubricant by its solvating effect on an insoluble (resin) matrix to which charged groups have been covalently bound. The solvating effects are measured electronically as a variation in conductivity or capacitance of the resin matrix with respect to temperature. The apparatus includes a metal mesh housing containing e.g. milligram amounts of charged resin beads. A metal probe is fitted in the containing mesh and makes contact only with the resin beads. The entire device is immersed in the lubricant and the electrical conductivity or capacitance is measured from the probe to the mesh through the resin beads. Lubricant degradation is measured as e.g. a decrease in electrical conductivity through the resin beads with respect to an increase in the lubricant's solvent polarity.

23 Claims, 2 Drawing Sheets

METHOD AND APPARATUS FOR FLUID QUALITY SENSING

BACKGROUND OF THE INVENTION

1. Field of Invention

This invention relates to measurement and testing for liquid analysis, and more particularly to determining electrically the quality of any natural or synthetic oil, oil substitute, oil additive, or any other nonpolar or weakly polar liquid.

2. Description of the Prior Art

Three well known methods of determining e.g. lubricating oil quality are infrared spectroscopy, pH measurement, and prediction of degradation. Measuring the quality of the oil by infrared spectroscopy has the advantage of determining many qualities of the oil other than lubricity. Unfortunately this method requires removing a sample of the oil from e.g. the automobile and placing it in an infrared spectroscopy instrument. The instrument is expensive and requires some dexterity and experience with scientific measurements to use. Thus this is not a suitable method for alerting one that the oil needs to be changed.

Although the pH of an oil gives an indication that something is wrong with the oil, the pH does not directly measure the oil lubricating quality, but merely measures the presence of acids in the oil. It does not determine that the oil has degraded if the oil is contaminated by water or metal particulate. Basing oil quality on pH can also be unreliable. Volatile acids can evaporate over extended periods at operating temperatures and give a pH reading inconsistent with oil quality. The pH sensor apparatus is expensive and not particularly suited for the environment of the oil pan of an internal combustion engine.

Prediction methods for oil degradation are simple. Based on the mileage of the vehicle, a light comes on telling one that the oil needs to be changed. This does not take into account the various qualities of oil that can be used, nor does it take into account the actual driving conditions that directly effect the oil condition. Further, it does not account for engine wear as a factor in oil degradation. This method has recently become more sophisticated; however it is still simply a prediction that provides no qualitative or quantitative information regarding actual oil condition.

SUMMARY OF THE INVENTION

In accordance with the invention, a method and apparatus determine the quality of a fluid (e.g. oil) by its solvating effect on an insoluble (resin) matrix to which charged groups have been covalently bound. The solvating effect is measured electronically as a variation in an electrical characteristic (e.g., capacitance or conductivity) of the matrix. The apparatus includes a conductive mesh containing small (milligram) amounts of charged resin beads. A metal probe is fitted in the mesh and makes contact with the resin. The entire device is immersed in the fluid, and electrical conductivity is measured from the probe to the mesh through the resin. Fluid quality degradation is measured as a change in electrical conductivity or capacitance through the resin with respect to an increase in the fluid's solvent polarity.

This invention therefore relates to a fluid quality sensing device and related method that determine, under actual operating conditions and in real time, the fluid quality. This cost-effective sensor is suitable for many applications in which oil or other fluids are used and where the quality of the fluid degrades over time.

The present invention more broadly has application where any nonpolar fluid or weakly polar fluid is used for purposes such as providing force, as would be the case in e.g. hydraulic hoists, or in heating or cooling applications such as heat exchangers, both instances involving a degradation of the relevant quality of the fluid with use. In addition, the invention has application to engines, transmissions, differentials, power steering units and hydraulic brake cylinders on vehicles such as cars, trucks, motorcycles, boats, tractors, and airplanes, and to stationary devices such as generators, turbines and pumps where a fluid is used for e.g. heating, cooling or transmitting force. The apparatus is placed in any location of a system which uses a fluid which degrades or where there is a need to determine fluid quality.

In a process in accordance with this invention, a support (solvated resin beads in one embodiment) holding charged groups serves as a conductor or capacitor between two electrodes. A change in electrical conductivity (or capacitance) results when the interactive behavior between the charged groups on the resin beads adjusts to changing solvent polarity conditions of a surrounding fluid. In a non-polar fluid environment, such as a clean oil being the fluid, neighboring charged groups orient themselves to a self-aggregated state and form clusters similar to a reverse micelle, analogous to detergent molecules in nonaqueous solvents.

The ionic attraction between neighboring charged groups in the resin beads serves as electro-chemical bridges and facilitates electrical transfer and can be measured as an increase in conductivity or a decrease in resistance (or change in capacitance). As the polarity of the fluid increases, indicating fluid degradation, the charged groups no longer form as tight a series of bridged clusters, which results in less efficient electrical transfer and consequently changes the electrical characteristic (lower conductivity or higher resistivity or a change in capacitance). The sensitivity of the method depends on a combination of the following resin characteristics: the percent crosslinking, the titer, the counter-ion, and the particle size of the beads. A series of conductivity (or resistivity) measurements can be plotted as a function of fluid temperature to form a smooth curve which can be described by an equation and used to estimate fluid degradation over a range of temperatures. Although one embodiment of this invention uses polystyrene resin beads as the support, any solvating, insoluble matrix may be used as the support.

More generally, this process measures the change in an electrical characteristic of a medium that is modified by the degradation in quality of surrounding fluid over a range of temperatures; the above described ion exchange resin material is used one embodiment.

Oil is an exemplary nonpolar fluid composed of long chain hydrocarbons having charged ends. Natural oil contains additional unsaturated components (double bonds called olefins) within the long hydrocarbon chain which, under appropriate conditions can begin to slowly oxidize. Synthetic oil has the advantage of not having these olefins, which is why it, in theory, lasts longer. However, even synthetic oil quality can suffer from wear. The quality of any oil suffers from a worn engine. Nitrogen oxides can react with unburned olefins (introduced into the oil as unburned gasoline from valve blow-by) to eventually form sludge. As oil degrades (due either to breakdown or contamination) its solvent properties change from a nonpolar nature to a polar one. Non-polar herein refers generally to a dielectric constant less than 15.

The present invention in one embodiment provides continuous real-time feedback as to the quality of the fluid (oil) used in, for example, an internal combustion engine. An apparatus in accordance with this invention includes an electrically conducting probe placed in a contact with a support (e.g., a quantity of polystyrene resin beads that are contained by a stainless steel mesh). The mesh is further contained by a structural housing that allows a liquid to flow through the mesh but does not allow the resin beads to escape. The electrical characteristics of the system between the probe and the conductive mesh vary in a direct relationship with the oil quality. For instance, clean oil provides greater conductance then contaminated oil. The level of contamination is determined due to the analog nature of the variable conductance or capacitance.

Although one embodiment of the apparatus in accordance with this invention attaches to the portion of an oil drain plug which resides inside an engine oil pan, the apparatus may be mounted in any position that contacts a sufficient quantity of the fluid in question to effect the sensor. Alternative locations for the oil sensor embodiment are the oil filter, oil pan, engine block or any other location where there is sufficient quantity of oil which is a representative sample of the oil within the engine.

The signal measured across the probe and the steel mesh is conditioned in one embodiment by a voltage divider circuit which allows a change in conductance to be converted to a change in voltage output. The signal is then isolated from any loading effects of a measuring device by a high input impedance, operational amplifier configured as a voltage follower.

The output signal of the circuit indicates the quality of the oil by different methods. For instance, the output can be supplied to a single LED, to multiple LED's, to an analog gauge or to a microprocessor. Since microprocessors and microcontrollers are used extensively in such applications as automobile control and display systems, the output signal from the oil quality sensor is easily adapted to function as an integral part of such a system.

DETAILED DESCRIPTION OF THE INVENTION

Figure 1:
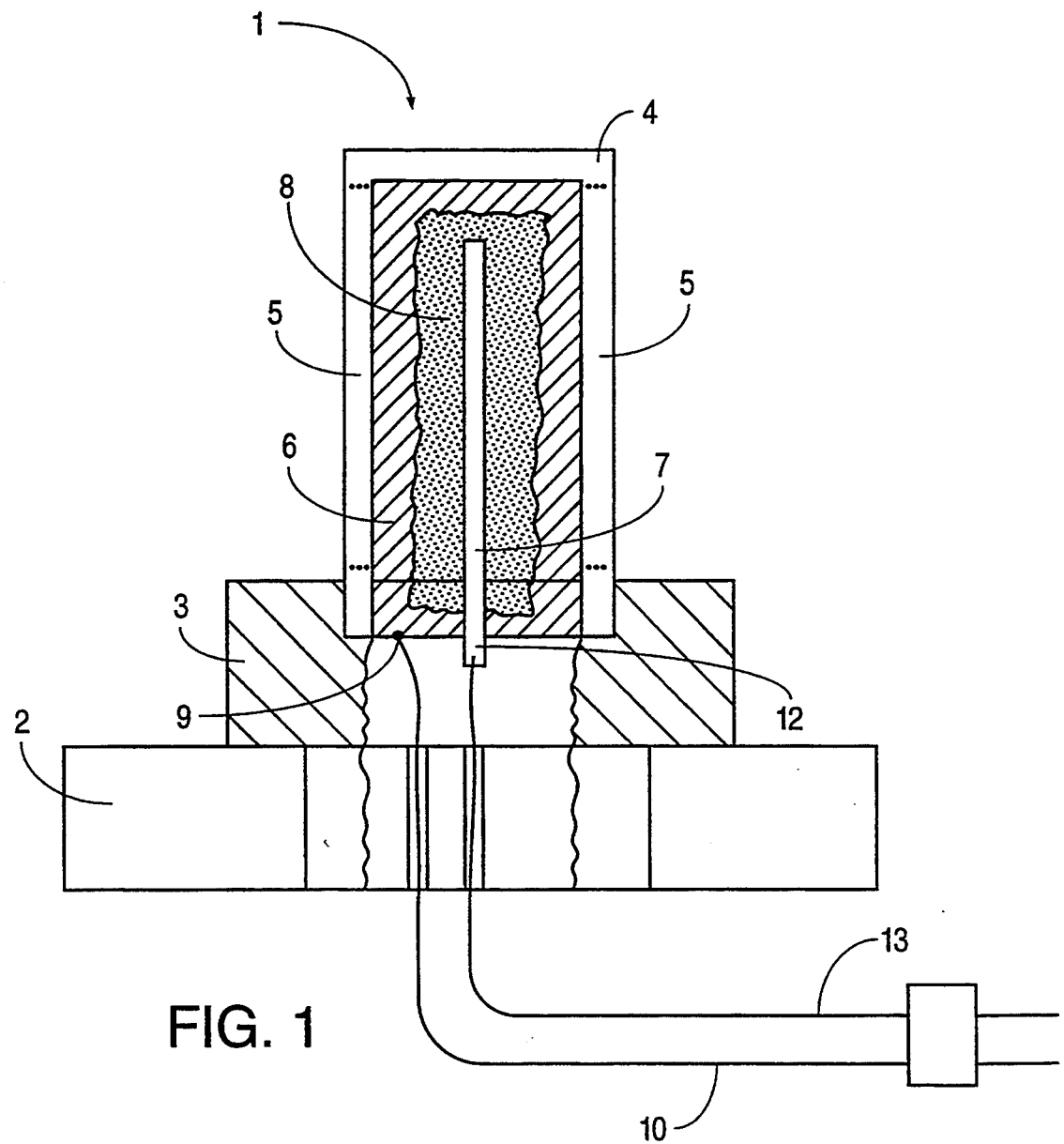
FIG. 1 is a cross-sectional view of an oil quality sensor assembly.

FIG. 1 shows a cross-sectional view of one embodiment of the oil quality sensor 1 mounted in an otherwise conventional drain plug 2 used in the oil pan of an internal combustion engine. The drain plug 2 with its standard hex nut arrangement and associated threaded surface 3 are shown as the chief mounting for the oil quality sensor. The e.g. plastic housing 4 provides the outer containment for conventional stainless steel wire mesh 6, which in turn holds the polystyrene resin beads 8 impregnated with the charged groups, in one embodiment sodium as the cation and sulfite as the anion, with the sulfite covalently bound to the beads. A typical amount of resin beads is 500 mg. The polystyrene beads are typically crosslinked with 8% divinylbenzene and contain a titer or exchange capacity of 1.7 meq/ml, each bead being of typically 200–400 mesh diameter.

Such resin beads are commercially available from Bio Rad Laboratories. Other suitable cation exchange groups are salts (e.g. sodium, ammonium) of polyatomic anions such as phosphates or carboxylates. Conversely, the exchange group may be anionic and include salts (e.g. chloride, acetate) of N-alkylated amines such as primary, secondary, or tertiary substituted analogs. More generally, cation exchangers or anion exchangers are used for the chemically active material; either strong or weak ion exchangers are suitable.

Opening 5 allows oil to flow through the mesh 6 and the resin beads 8. A similar opening is on the opposite side of the housing 4, thus allowing a flow-through arrangement. The metal probe 7 is one electrode of the electrical circuit for measuring the desired electrical characteristic through the resin matrix. Wire 13 is connected at point 12 and routed to the external plug 11 via a conventional oil-tight seal (not shown). Wire 10 is connected to the mesh 6 at point 9 and routed to the external plug 11, also via an oil-tight seal (not shown). It can be seen that the mesh is the second electrode of the electrical circuit for measuring the electrical characteristic through the resin matrix. Plug 11 connects the sensor to the external signal conditioning circuit.

Figure 2:
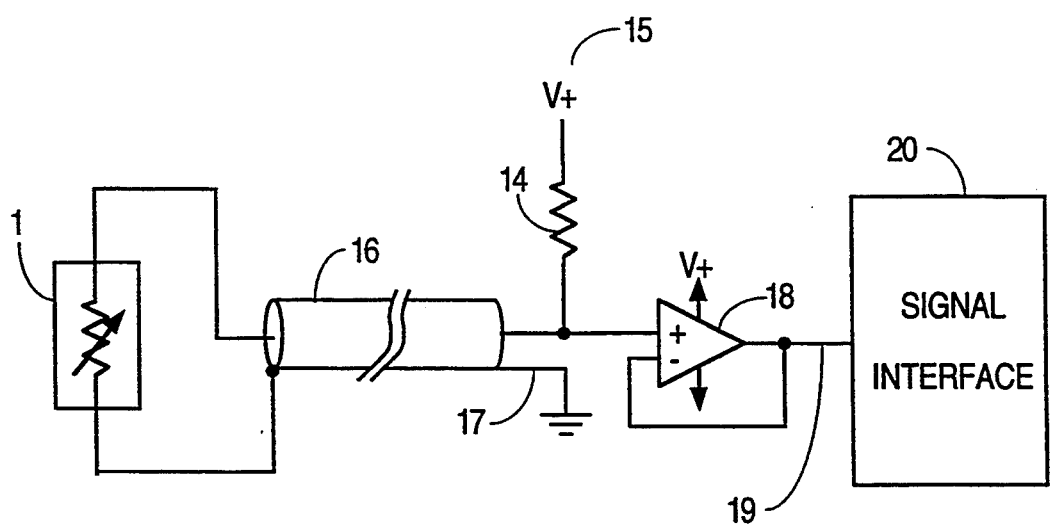
FIG. 2 is a schematic diagram of the oil quality sensor assembly and associated circuitry.

FIG. 2 is a schematic diagram of the oil quality sensor system, here measuring conductivity. The positive voltage $V+$ at node 15 causes an electric current to flow through a voltage divider consisting of resistor 14 and sensor element 1. The coaxial cable 16 reduces the effect of outside electrical noise on the signal from the remotely located sensor element 1. The resulting voltage developed across the sensor element 1, which is referenced to voltage $V+$, is applied to the noninverting input of the voltage follower 18.

Voltage follower 18 is a high input impedance amplifier, such as an RCA CA3140 integrated circuit. Such a voltage follower is used because of the very high impedance exhibited by the sensor element under normal operating conditions, and any loading of the circuit by an external measuring means would affect the accuracy of subsequent voltage readings.

The voltage output at node 19 from voltage follower 8 is shown applied to a conventional signal interface circuit 20. The signal interface circuit illustrated is generic in nature, since its function is highly dependent on the application. It is, in one case, a simple analog meter which displays a voltage representing oil quality, where a low voltage reading is an indication of good oil quality and a higher voltage reading is an indication of poor oil quality. In another case the signal interface circuit is an analog to digital converter whose output is supplied to a microprocessor system for further conditioning and subsequent output to a display for indicating the oil quality. A further advantage of the circuit shown in FIG. 2 is that, in the event of a breakage of the coaxial cable 16 or the failure of the sensor element 1 in an open circuit condition, the output voltage 19 will essentially go to the $V++$ level, thus indicating a system failure condition.

The method and apparatus disclosed herein allow real time, continuous measurement of the actual quality of the lubricant, including lubricating ability. Contamination of the oil by water or metal particulate is sensed, thereby measuring general wear of the oil. The vehicle user will thereby have an indicator of the quality of the oil including an indication that the oil is no longer lubricating the engine properly. This method optimizes the use of the oil, because the oil need not be changed when it is still in an acceptable lubricating condition. The method further optimizes the wear of the engine since it gives direct feedback to the user that the engine is being damaged by worn out oil.

Due to the temperature dependent nature of the sensor output, it can be used as an indicator of oil temperature. Likewise, with proper conditioning of the output from the sensor, it can be used to measure the absolute presence or absence of oil. In addition, by determining the rate of degradation of the oil, this sensor gives an indication of general condition of the engine. This can be refined when combined with a prediction method. Finally, since the solvating effect of the oil on the insoluble matrix is essentially a unilateral process, the sensor element is replaced when the oil quality has reached the point where the oil must be replaced. Because the cost of the sensor element is low, its replacement cost is acceptable.

Alternative embodiments in accordance with the invention include use of a porous material such as a sintered metal or porous bronze instead of the mesh to hold the resin (support). The support may be, instead of beads, a sheet or other configuration. More generally, any insoluble matrix may be used having ionic properties that conducts a charge for the active element of the sensor. Alternative configurations of the housing and mesh include a mesh molded into a plastic housing; the electrode probe is in one version also part of the housing.

Figure 3:
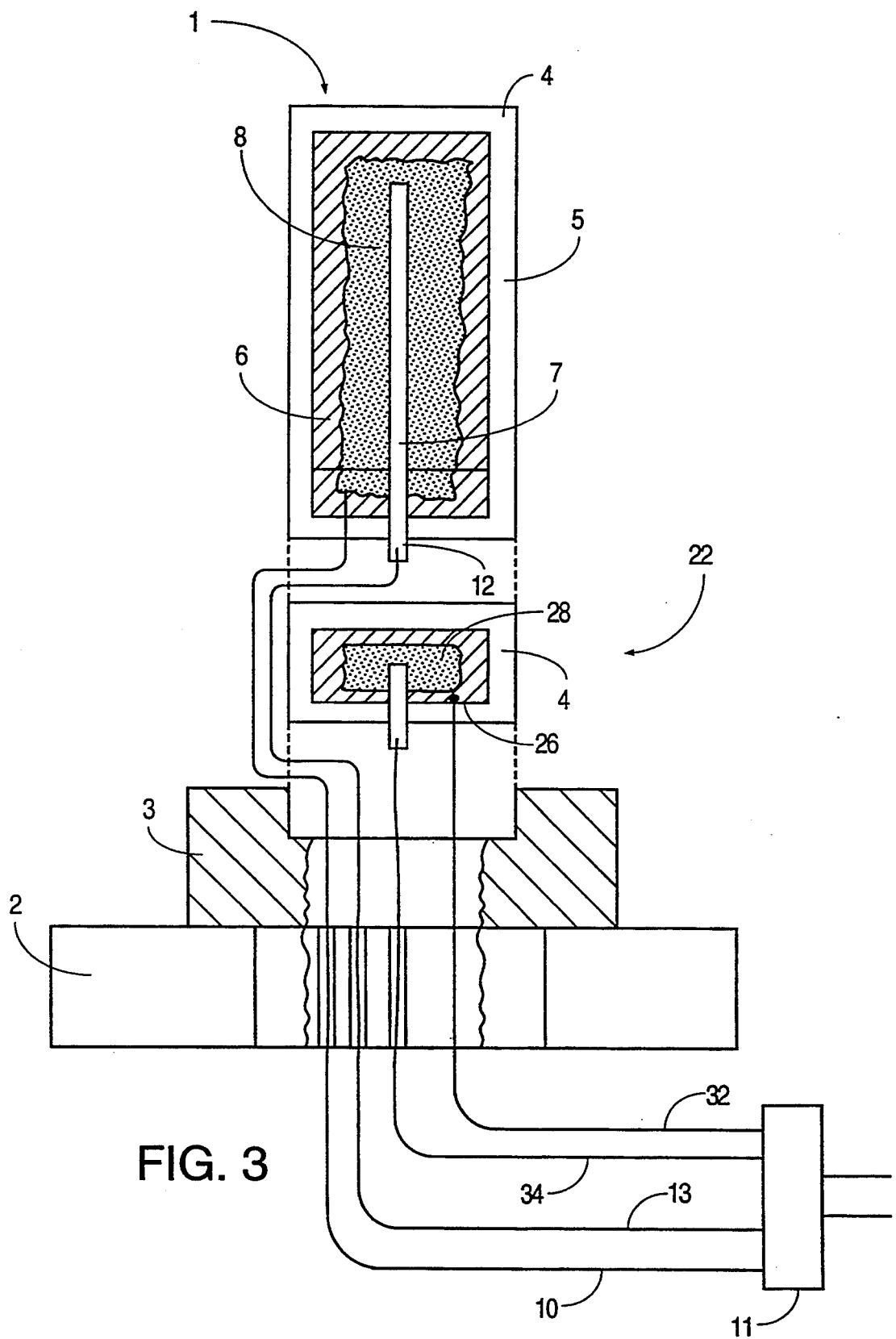
FIG. 3 is a cross-sectional exploded view of an oil quality sensor assembly in accordance with a second embodiment of the present invention.

An additional embodiment of the device (see FIG. 3 which shows in an exploded view a number of elements identical to and having the same reference numerals as in FIG. 1 plus the internal standard) includes an internal standard 22. This internal standard 22 includes a separate smaller sensor device 26 (holding similar charged resin 28) contained within the housing 4 of the main sensor device (except for the external standard output leads 32, 34) and sealed to the environment with clean fluid 36 inside so as to prevent contamination by the larger body of degrading fluid. In this manner a direct comparison in terms of relative oil degradation can be made. The internal standard allows the device to function also as a temperature sensor independent of fluid degradation. For instance, a change of the electrical characteristics of the clean fluid in the internal standard would provide an indication of temperature, while a change in the electrical characteristics of the degrading fluid provides the indication of fluid quality.

This disclosure is illustrative and not limiting; further modifications will be apparent to one skilled in art in the light of this disclosure and are intended to fall within the scope of the appended claims.

We claim:

1. A fluid sensor comprising:
    a housing;
    a support holding charged groups and being in the housing;
    a first electrode and a second electrode in the housing and in contact with the support; and
    at least one opening in the housing for admitting fluid into the housing.

2. The fluid sensor of claim 1, wherein the support comprises resin beads impregnated with the charged groups.

3. The fluid sensor of claim 2, further comprising a conductive mesh for holding the beads, wherein the conductive mesh is the first electrode.

4. The fluid sensor of claim 1, wherein the charged groups include an anion and cations.

5. The fluid sensor of claim 1, further comprising a drain plug in which the housing is mounted.

6. The fluid sensor of claim 1, further comprising output circuitry connected between the first and second electrodes for displaying a signal indicative of a voltage between the electrodes.

7. The fluid sensor of claim 1, further comprising a second fluid sensor including a second support holding charged groups in a second housing, a first and a second electrode in the second housing and in contact with the second support, and a second fluid in the second housing;
    wherein the second fluid sensor is inside the housing of the first fluid sensor.

8. The fluid sensor of claim 1, wherein the fluid is a non-polar fluid.

9. The fluid sensor of claim 1, wherein the fluid is a weakly polar fluid.

10. A drain plug fluid sensor comprising:
    a drain plug structure adapted to fitting in a drain hole of a fluid reservoir and defining a passage communicating with the reservoir;
    a housing extending from the drain plug structure and having an internal cavity connecting to the passage;
    a support holding charged groups and being in the internal cavity; and
    a first electrode and a second electrode in the internal cavity and in contact with the support.

11. A method for measuring an electrical characteristic of a non-polar or weakly polar fluid, comprising the steps of:
    providing an ion-exchange resin material having a plurality of charged groups in clusters and having electro-chemical bridges between the charged groups in each cluster;
    circulating the non-polar or weakly polar fluid to contact the material; and
    measuring an electrical characteristic of the material while the fluid is circulating.

12. The method of claim 11, further comprising the step of conditioning the measured electrical characteristic to provide an indication of a property of the fluid.

13. The method of claim 11, wherein the fluid is a working fluid in a system, and the step of circulating is during a normal operation of the system.

14. The method of claim 11, wherein the electrical characteristic is electrical conductivity.

15. A method of determining a quality of a fluid, comprising the steps of: providing an insoluble support holding charged groups;
    circulating the fluid to contact the support; and
    measuring a solvating effect on the charged groups of the fluid as a variation in an electrical characteristic of the support.

16. The method of claim 15, wherein the fluid is a non-polar fluid.

17. The method of claim 15, wherein the fluid is a weakly polar fluid.

18. The method of claim 15, wherein the support is a quantity of resin beads.

19. The method of claim 18, wherein the resin beads are held within a conductive mesh.

20. The method of claim 15, wherein the fluid is an operating fluid in a system, and the step of circulating is during normal operation of the system.

21. The method of claim 15, wherein the electrical characteristic is conductivity.

22. The method of claim 15, wherein the electrical characteristic is capacitance.

23. The method of claim 15, further comprising the steps of:
   providing a second insoluble support holding charged groups;
   providing a second fluid in contact with the second insoluble support; and
   measuring a solrating effect on the charged groups of the second fluid due to temperature changes as a variation in an electrical characteristic of the second support.

* * * * *

UNITED STATES PATENT AND TRADEMARK OFFICE
CERTIFICATE OF CORRECTION

PATENT NO.    :  5,435,170
DATED         :  July 25, 1995
INVENTOR(S)   :  Paul J. Voelker and Joe D. Hedges It is certified that error appears in the above-identified patent and that said Letters Patent is hereby corrected as shown below:

Column 3, line 5, delete "15" and insert --15--.
Column 8, line 7, delete "solrating" and insert --solvating--.

Signed and Sealed this

Tenth Day of October, 1995

*Attest:*

BRUCE LEHMAN

*Attesting Officer*  *Commissioner of Patents and Trademarks*